(12) United States Patent
Allcock et al.

(10) Patent No.: US 7,763,702 B2
(45) Date of Patent: Jul. 27, 2010

(54) SYNTHESIS OF POLYPHOSPHAZENES WITH SULFONIMIDE SIDE GROUPS

(75) Inventors: Harry R. Allcock, State College, PA (US); Michael A. Hofmann, Brookhaven, PA (US); Catherine M. Ambler, State College, PA (US); Maher E. Andrew, Little Britian (CA); Richard M. Wood, State College, PA (US); Daniel T. Welna, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 733 days.

(21) Appl. No.: 11/783,880

(22) Filed: Apr. 12, 2007

(65) Prior Publication Data

US 2007/0265426 A1      Nov. 15, 2007

Related U.S. Application Data

(63) Continuation-in-part of application No. 10/779,483, filed on Feb. 13, 2004, now abandoned.

(60) Provisional application No. 60/450,178, filed on Feb. 13, 2003.

(51) Int. Cl.
| | |
|---|---|
| *C08G 79/02* | (2006.01) |
| *C07C 311/48* | (2006.01) |
| *C07C 311/49* | (2006.01) |
| *B01D 67/00* | (2006.01) |
| *B01D 71/34* | (2006.01) |
| *C08J 5/20* | (2006.01) |
| *C08J 5/22* | (2006.01) |
| *C08L 85/02* | (2006.01) |
| *H01M 8/10* | (2006.01) |

(52) U.S. Cl. .................. 528/399; 528/391; 528/398; 528/89; 528/488; 525/538; 525/540; 525/92 J; 525/334.1; 525/242; 524/80; 429/122; 564/83

(58) Field of Classification Search ............... 528/399, 528/398, 391, 89, 488; 525/538, 540, 92 J, 525/334.1, 242; 524/80; 429/122; 564/83
See application file for complete search history.

(56) References Cited

U.S. PATENT DOCUMENTS

| | | | | |
|---|---|---|---|---|
| 4,107,146 | A * | 8/1978 | Dieck et al. ............... 528/168 |
| 4,242,499 | A * | 12/1980 | Allcock et al. ............. 528/399 |
| 5,457,160 | A * | 10/1995 | Allcock et al. ............. 525/188 |
| 5,747,604 | A * | 5/1998 | Allcock et al. ............. 525/417 |
| 6,365,294 | B1 * | 4/2002 | Pintauro et al. ............ 429/33 |

* cited by examiner

*Primary Examiner*—Duc Truong
(74) *Attorney, Agent, or Firm*—Law Offices of John Parrish

(57) ABSTRACT

The invention relates to sulfonimide bearing phenolic compounds and the use of those compounds to produce polyphosphazenes functionalized by one or more of those compounds alone, or in combination with cosubstituents. The invention also relates to blends of sulfonimide functionalized phosphazene polymers with other polymers, membranes formed of the functionalized polymers, and the use of those membranes in devices such as fuel cells.

4 Claims, No Drawings

SYNTHESIS OF POLYPHOSPHAZENES WITH SULFONIMIDE SIDE GROUPS

This application is a continuation in part of application Ser. No. 10/779,483 filed on Feb. 13, 2004 now abandoned which claims priority to U.S. patent application 60/450,178 filed Feb. 13, 2003.

GOVERNMENT SPONSORSHIP

This work was supported by U.S. Department of Energy, grant number DE-FC36-01GO11085.

FIELD OF THE INVENTION

The present invention relates to phenolic sulfonimides and to ion conducting phosphazene polymers functionalized with those groups.

BACKGROUND OF THE INVENTION

Proton conductive polymers are attractive materials for use in applications such as polymer electrolyte fuel cells (PEFCs) for power generation. However, the types of proton conductive polymers which may be used as membranes in PEFCs is limited by demanding membrane requirements such as good chemical and mechanical stability, high ionic conductivity, and low reactant permeability (i.e. hydrogen or methanol, and oxygen).

The art has focused on membranes made from sulfonic acid functionalized polymers, in particular, membranes such as Nafion™ formed from perfluorosulfonic acid functionalized polymers.

Attractive alternatives to sulfonic acid containing materials for use in membranes include sulfonimide groups. The high acid strength of sulfonimide acids is well known. DesMarteau et al., *J. Fluorine Chem.* 1995, 72, 203-208 and U.S. Pat. No. 5,463,005, prepared perfluorinated polymeric membranes containing sulfonimide acid groups. DesMarteau et al. also described synthesis of trifluorovinyl aromatic ether monomers functionalized with both pendent sulfonimide groups as well as sulfonimide groups incorporated into the monomer main chain. These monomers undergo thermal cyclopolymerization to yield perfluorocyclobutane aromatic polyethers.

Sulfonimide-functionalized polymers which include aromatic units also have been developed. Feiring et al. synthesized a styrene monomer functionalized by a pendent sulfonimide group. Feiring et al. also homopolymerized and copolymerized the functionalized styrene monomer with a variety of olefinic monomers for potential use as electrolytes in lithium batteries.

Polyphosphazenes are a class of polymers which contain a flexible backbone of —P=N— repeating units and two organic, inorganic, or organometallic groups attached to each phosphorus atom. Polyphosphazenes have a phosphorous-nitrogen sequence with organic substituents on the phosphorous atom as follows:

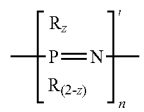

where $R_z$ and $R'_{(2-z)}$ are the same or different organic substituents and $0<z<2$.

These polymers can be prepared by the thermal ring opening polymerization of hexachlorocyclotriphosphazene or by the living cationic polymerization of phosphoranimines to form poly(dichlorophosphazene) which is employed as a reactive macromolecular intermediate. The chlorine atoms in this polymer can be replaced via nucleophillic substitution reactions using, for example, alkoxy, aryloxy or amino reagents to give stable poly(organophosphazene) derivatives.

Incorporation of carboxylic, phosphonic, and sulfonic acids into polyphosphazenes is known. Polyphosphazenes functionalized with phosphonic and sulfonic acid groups have been shown to be promising as fuel cell membrane materials, particularly for use in direct methanol fuel cells (DMFCs). See J. Membrane Science, Vol. 119, pg 155 (1996) and Vol. 154, pg. 175 (1999)).

These functionalized polyphosphazene polymers are obtained by treating poly(aryloxyphosphazenes) with relatively harsh reagents such as $SO_3$ to incorporate the acidic functionality. This method limits the choice of functional side groups and thus the degree of tailorability of the phosphazene polymer. Sodium salts of difunctional reagents such as p-hydroxybenzenesulfonic acid are, in general, not suitable reagents for reaction with unsubstituted or partially substituted poly(dichlorophosphazene) due to the tendency of both of the functional sites of the difunctional reagent to cause polymer crosslinks and insoluble products.

A need therefore exists for having the acid functionality incorporated into a side group which then can be reacted with the polyphosphazene or partially substituted derivatives of polyphosphazene.

SUMMARY OF THE INVENTION

The invention relates to compounds of the formula $ROC_6H_4SO_2NMSO_2R_f$ where R is a $C_1$-$C_5$ alkyl, Li, Na, H and K, and where M is any consisting of H, Li, K, Na, $R'_3NH^+$, where R' is a $C_1$-$C_5$ alkyl, or mixtures thereof, and where $R_f$ is any $C_1$-$C_8$ perfluoroalkyl; compounds of the formula $ROC_6H_4SO_2NR^1SO_2R_f$ where R is a $C_1$-$C_5$ alkyl where $R^1$ is Li, K, H or Na and where $R_f$ is any $C_1$-$C_8$ perfluoroalkyl; sulfonimide bearing compounds of the formula $R^1OC_6H_4SO_2NR^1SO_2R_f$ where $R^1$ is Li, K, H, or Na and, where $R_f$ is any $C_1$-$C_8$ perfluoroalkyl; alkali sulfonimide bearing compounds of the formula $ROC_6H_4SO_2NR^1SO_2R_f$ where R and $R^1$ are the same or different and each of R and $R^1$ may be Li, Na, H or K, preferably R and $R^1$ each are Na, and, where $R_f$ is any $C_1$-$C_8$ perfluoroalkyl; amine terminated sulfonimide bearing compounds of the formula $H_2NC_6H_4SO_2NR^1SO_2R_f$ where $R^1$ is Li, Na, K, or H, preferably Na, or $R'_3NH^+$, where R' is a $C_1$-$C_5$ alkyl, and where $R_f$ is any $C_1$-$C_8$ perfluoroalkyl.

The invention also relates to manufacture of sulfonimide bearing compounds of the formula $R^1OC_6H_4SO_2NR^1SO_2R_f$, where $R_1$ is Na, Li, H, or K, and, where $R_f$ is any $C_1$-$C_8$ perfluoroalkyl. Manufacture of these sulfonimides entails reacting $ROC_6H_4SO_2Cl$ where R is $C_1$-$C_5$ alkyl with $R_fSO_2NH_2$, where $R_f$ is any $C_1$-$C_8$ perfluoroalkyl, and a base such as Trimethylamine, Triethylamine, Pyridine, Imidazole, Pyrimidine or mixtures thereof in the presence of a solvent such as Acetone, Acetonitrile, N,N-dimethylacetamide, N,N-dimethylformamide, Dimethyl sulfoxide, Hexamethylphosphoramide, Nitromethane, Pyridine, Tetrahydrofuran or mixtures thereof to produce a first intermediate compound of the formula $ROC_6H_4SO_2NMSO_2R_f$ where M is any of H, Li, K, Na, $R'_3NH+$ where R' is $C_1$-$C_5$ alkyl, or mixtures thereof. The first intermediate compound is reacted with an alkali metal salt such as Lithium methoxide, Lithium ethoxide, Lithium tert-butoxide, Lithium phenolate, Lithium hydroxide, Sodium methoxide, Sodium ethoxide, Sodium tert-butoxide, Sodium phenolate, Sodium hydroxide Potassium methoxide, Potassium ethoxide, Potassium phenolate, Potassium tert-butoxide, Potassium hydroxide or mixtures thereof in the presence of a solvent such as Methanol, Ethanol, Isopropanol, tert-Butanol, Acetone, Acetonitrile, N,N-dimethylacetamide, N,N-dimethylformamide, Dimethyl sulfoxide, Hexamethylphosphoramide, Nitromethane, Tetrahydrofuran or mixtures thereof to produce a second intermediate compound of the formula $ROC_6H_4SO_2NMSO_2R_f$ where M is Li, Na or K, and R is a $C_1$-$C_5$ alkyl, and where $R_f$ is any $C_1$-$C_8$ perfluoroalkyl. The second intermediate is reacted with an alkali alkyl thiolate any of sodium ethane thiolate, lithium ethane thiolate, potassium ethane thiolate and mixtures thereof to produce a sulfonimide bearing compound of the formula $R^1OC_6H_4SO_2NR^1SO_2R_f$, where $R^1$ is Li, Na, H, or K or mixtures thereof, and where $R_f$ is any $C_1$-$C_8$ perfluoroalkyl.

The invention also relates to the manufacture of the amine form of the sulfonimide structure, as represented by $NH_2C_6H_4SO_2NR^1SO_2R_f$, where $R^1$ is Na, Li, K, or H, and where $R_f$ is any $C_1$-$C_8$ perfluoroalkyl. This is accomplished by reacting $HOC_6H_4SO_2NR^1SO_2R_f$ with tosyl chloride in a solvent such as dichloromethane in the presence of a tertiary amine such as triethyl amine, followed by reaction with ammonia to yield a product $NH_2C_6H_4SO_2NR^1SO_2R_f$.

Another aspect of the invention relates to methods of manufacture of phenoxy sulfonimide functionalized polyphosphazenes. In a first aspect, the method entails reacting a polyphosphazene of the formula $(NPCl_2)_n$, where $n \geq 3$ with an alkali oxide derivative such as $R^1OC_6H_4CH_3$ where $R^1$ is Li, Na, K, or mixtures thereof, to produce a first intermediate of the formula $[NP(Cl)_x(OC_6H_4CH_3)_{(2-x)}]_n$ where $n \geq 3$. The first intermediate is reacted with a second alkali salt such as $R^1OC_6H_4SO_2NR^1SO_2R_f$, where $R^1$ is Li, Na, K, or mixtures thereof and where $R_f$ is any $C_1$-$C_8$ perfluoroalkyl, to produce a second intermediate of the formula such as $[NP(OC_6H_4SO_2NR^1SO_2R_f)_x(OC_6H_4CH_3)y(Cl)_{2-x-y}]n$ where x is $\leq 2$ and y is $\leq (2-x)$. The second intermediate is reacted with a third alkali salt such as $R^1OC_6H_4CH_3$, where $R^1$ is Li, Na, K, or mixtures thereof, to produce a phenoxy sulfonimide functionalized polyphosphazene of the formula such as $[NP(OC_6H_4SO_2NR^1SO_2R_f)_x(OC_6H_4CH_3)_{2-x}]n$ where $R^1$ is Li, K, H or Na, preferably Na and where x is $\leq 2$.

In another aspect, manufacture of a phenoxy sulfonimide functionalized polyphosphazene entails reacting a polyphosphazene of the formula $(NPCl_2)_n$ where $n \geq 3$ with an alkali oxide such as $R^1OC_6H_4CH_3$ and with $R^1OC_6H_4SO_2NR^1SO_2R_f$ where $R^1$ is Na, K or Li and where $R_f$ is any $C_1$-$C_8$ perfluoroalkyl to produce a reaction product and reacting the reaction product with a second alkali oxide such as $R^1OC_6H_4CH_3$, where $R^1$ is Li, Na, H, K, or mixtures thereof, to produce a phenoxy sulfonimide functionalized polyphosphazene of the formula such as $[NP(OC_6H_4SO_2NR^1SO_2R_f)_x(OC_6H_4CH_3)_{2-x}]n$ where x is $\leq 2$.

Another embodiment of the invention relates to manufacture of variation s of phenoxy sulfonimide functionalized polyphosphazenes. In a first aspect, the method entails reacting a polyphosphazene of the formula $(NPCl_2)_n$, where $n \geq 3$ with an alkali oxide derivative $R^1Y$, where Y may be an alkoxy, aryloxy, fluorinated or perfluorinated alkoxy or aryloxy, halogenated or functionalized alkoxy or aryloxy, or mixtures thereof, and where $R^1$ is Li, Na, K, or mixtures thereof, to produce a first intermediate of the formula $[NP(Cl)_x(Y)_{2-x}]_n$ where $n \geq 3$. The first intermediate is reacted with a second alkali salt such as $R^1OC_6H_4SO_2NR^1SO_2R_f$ where $R^1$ is Li, Na, K, or mixtures thereof, and where $R_f$ is any $C_1$-$C_8$ perfluoroalkyl, to produce a second intermediate of the formula such as $[NP(OC_6H_4SO_2NR^1SO_2R_f)_x(Y)y(Cl)_{2-x-y}]n$ where x is $\leq 2$ and where y is $\leq (2-x)$. The second intermediate is reacted with a third alkali oxide derivative $R^1Y$, where Y may be an alkoxy, aryloxy, fluorinated or perfluorinated alkoxy or aryloxy, halogenated or functionalized alkoxy or aryloxy, or mixtures thereof, and where $R^1$ is Li, Na, K, or mixtures thereof, to produce a phenoxy sulfonimide functionalized polyphosphazene of the formula such as $[NP(OC_6H_4SO_2NR^1SO_2R_f)_x(Y)_{2-x}]n$ where $R^1$ is Li, K, H or Na, preferably Na and where x is $\leq 2$.

In another aspect, manufacture of a phenoxy sulfonimide functionalized polyphosphazene entails reacting a polyphosphazene of the formula $(NPCl_2)_n$, where $n \geq 3$ with an alkali oxide derivative $R^1Y$, where Y may be an alkoxy, aryloxy, fluorinated or perfluorinated alkoxy or aryloxy, halogenated or functionalized alkoxy or aryloxy, or mixtures thereof, and where $R^1$ is Li, Na, K, or mixtures thereof, and with $R^1OC_6H_4SO_2NHSO_2R_f$ where $R^1$ is Na, K or Li and where $R_f$ is any $C_1$-$C_8$ perfluoroalkyl to produce a reaction product, and reacting the reaction product with a second alkali oxide derivative $R^1Y$, where Y may be an alkoxy, aryloxy, fluorinated or perfluorinated alkoxy or aryloxy, halogenated or functionalized alkoxy or aryloxy, or mixtures thereof, and where $R^1$ is Li, Na, K, or mixtures thereof, to produce a phenoxy sulfonimide functionalized polyphosphazene of the formula $[NP(OC_6H_4SO_2NR^1SO_2R_f)_x(Y)_{2-x}]n$ where x is $\leq 2$.

Another embodiment of the invention relates to alkali sulfonimide functionalized polyphosphazene homopolymers of the formula $[NP(OC_6H_4SO_2NR^2SO_2R_f)_2]_n$, where $R^2$ is Li, Na, H or K, preferably Na. The homopolymer is made by reacting $(NPCl_2)_n$, where $n \geq 3$ with $R^1OC_6H_4SO_2NR^1SO_2R_f$, where $R^1$ is any of Li, K and Na, and where $R_f$ is any $C_1$-$C_8$ perfluoroalkyl, at a temperature of about 60° C. to about 200° C. at a pressure of about ambient to 12 bar for about 12 hours to about 40 hours.

Another embodiment of the invention relates to manufacture of further variations of phenoxy sulfonimide functionalized polyphosphazenes. In a first aspect, the method entails reacting a polyphosphazene of the formula $(NPCl_2)_n$, where $n \geq 3$ with an amine derivative $NH_2Y$, where Y may be an alkyl such as $-CH_3$, $-CH_2CH_3$, $-CH_2CH_2CH_3$, $-CH_2CH_2CH_2CH_3$, aryl-$C_6H_5$, $-C_6H_4CH_3$, $-C_6H_4CH_2CH_3$, $-C_6H_4CH_2CH_2CH_3$, fluorinated alkyl such as $-CH_2CF_2CF_2CF_2CF_2H$, $-CH(CF_3)_2-CH_2CF_2CH(F)CF_3-CH_2CF_3-CH_2CF_2CF_2CF_3$, perfluorinated alkyl such as $-CF_3$, $-CF_2CH_3$, $-CF_2CF_2CF_2CF_3$, fluorinated aryl such as $-C_6F_5$, $-C_6H_4CF_3$, $-C_6H_3(CF_3)_2$, $-C_6H_4CH_2CF_3$, halogenated or functionalized alkyl or aryl as $-CH_2CH_2CH_2OTHP$, $-C_6H_4COOPr$, $-C_6H_4OTHP$, $-CH_2CF_2CF_2CF_2CF_2CH_2OTHP$, or mixtures thereof, to produce a first intermediate of the formula $[NP(Cl)_x(NHY)_{2-x}]_n$, where $n \geq 3$. The first intermediate is reacted with a second alkali salt such as $R^1OC_6H_4SO_2NR^1SO_2R_f$, where R1 is Li, Na, K, or mixtures thereof, and where $R_f$ is any $C_1$-$C_8$ perfluoroalkyl, to produce a second intermediate of the formula such as $[NP(OC_6H_4SO_2NR^1SO_2R_f)_x(NHY)y(Cl)_{2-x-y}]n$ where x is $\leq 2$ and where y is $\leq (2-x)$. The second intermediate is reacted with another amine derivative $NH_2Y$, where Y may be an Y may be an alkyl such as $-CH_3$, $-CH_2CH_3$, $-CH_2CH_2CH_3$, $-CH_2CH_2CH_2CH_3$, aryl-$C_6H_5$, $-C_6H_4CH_3$, $-C_6H_4CH_2CH_3$, $-C_6H_4CH_2CH_2CH_3$, fluorinated alkyl such as $-CH_2CF_2CF_2CF_2CF_2H$, $-CH(CF_3)_2-CH_2CF_2CH(F)CF_3-CH_2CF_3-CH_2CF_2CF_2CF_3$, perfluorinated alkyl such as $-CF_3$, $-CF_2CF_3$, $-CF_2CF_2CF_2CF_3$, fluorinated aryl such as $-C_6F_5$, $-C_6H_4CF_3$, $-C_6H_3(CF_3)_2$, —$C_6H_4CH_2CF_3$, halogenated or functionalized alkyl or aryl as —$CH_2CH_2CH_2OTHP$, —$C_6H_4COOPr$, —$C_6H_4OTHP$, —$CH_2CF_2CF_2CF_2CF_2CH_2OTHP$, or mixtures thereof, to produce a phenoxy sulfonimide functionalized polyphosphazene of the formula [$NP(OC_6H_4SO_2NR^1SO_2R_f)_x$ $(NHY)_{2-x}$] n where $R^1$ is Li, K, H or Na, preferably Na where x is $\leq 2$.

In another aspect, manufacture of a phenoxy sulfonimide functionalized polyphosphazene entails reacting a polyphosphazene of the formula $(NPCl_2)_n$ where $n \geq 3$ with an amine derivative $NH_2Y$, where Y may be an alkyl, aryl, fluorinated or perfluorinated alkyl or aryl, halogenated or functionalized alkyl or aryl, or mixtures thereof, and with $R^1OC_6H_4SO_2NHSO_2R_f$ where $R^1$ is Na, K or Li and where $R_f$ is any $C_1$-$C_8$ perfluoroalkyl, to produce a reaction product, and reacting the reaction product with a second amine derivative $NH_2Y$, where Y may be an alkyl such as —$CH_3$, —$CH_2CH_3$, —$CH_2CH_2CH_3$, —$CH_2CH_2CH_2CH_3$, aryl- $C_6H_5$, —$C_6H_4CH_3$, —$C_6H_4CH_2CH_3$, —$C_6H_4CH_2CH_2CH_3$, fluorinated alkyl such as —$CH_2CF_2CF_2CF_2CF_2H$, —$CH(CF_3)_2$—$CH_2CF_2CH(F)CF_3$—$CH_2CF_3$—$CH_2CF_2CF_2CF_3$, perfluorinated alkyl such as —$CF_3$, —$CF_2CF_3$, —$CF_2CF_2CF_3$, fluorinated aryl such as —$C_6F_5$, —$C_6H_4CF_3$, —$C_6H_3(CF_3)_2$, —$C_6H_4CH_2CF_3$, halogenated or functionalized alkyl or aryl as —$CH_2CH_2CH_2OTHP$, —$C_6H_4COOPr$, —$C_6H_4OTHP$, —$CH_2CF_2CF_2CF_2CF_2CH_2OTHP$, or mixtures thereof, to produce a phenoxy sulfonimide functionalized polyphosphazene of the formula such as [$NP(OC_6H_4SO_2NR^1SO_2R_f)_x$ $(NHY)_{2-x}$]n where x is $\leq 2$, which may then be converted to [$NP(OC_6H_4SO_2NHSO_2R_f)_x(NHY)_{2-x}$]n where x is $\leq 2$.

A still further embodiment of the invention relates to alkali phenoxy sulfonimide functionalized polyphosphazene copolymers of the formula [$NP(ZR^2)_x$ $(ZC_6H_4SO_2NR^1SO_2R_f)_{(2-x)}]_n$ where $n \geq 3$ and where x is $\leq 2$ and where $R^2$ may be an alkyl, aryl, fluorinated or perfluorinated alkyl or aryl, halogenated or functionalized alkyl or aryl, or mixtures thereof, Z is O or NH, and $R^1$ is Na, Li, H or K, preferably Na, and where $R_f$ is any $C_1$-$C_8$ perfluoroalkyl. The alkali phenoxy sulfonimide functionalized polyphosphazene copolymer may be made by reacting $(NPCl_2)_n$, where $n \geq 3$ with a first amount of compound of the formula $R^3R^2$ where $R^3$ is any of —NaO, —LiO, —KO, $NH_2$ or mixtures thereof, $R^2$ may be an alkyl, aryl, fluorinated or perfluorinated alkyl or aryl, halogenated or functionalized alkyl or aryl, or mixtures thereof, with a second amount of a compound of the formula $R^3C_6H_4SO_2NR^1SO_2R_f$ where $R^3$ is any of —NaO, —LiO, —KO, $NH_2$ or mixtures thereof, where $R_f$ is any $C_1$-$C_8$ perfluoroalkyl, and where $R^1$ is Na, Li, or K, or mixtures thereof, at a first temperature of about 60° C. to about 200° C. to produce a reaction product, and reacting the reaction product with $R^3R^2$ at a second temperature of 60° C. to about 200° C. at a pressure of about ambient to 12 bar.

The invention also relates to haloalkoxy sulfonimide functionalized polyphosphazenes of the formula [$NP(OCH_2(CF_2)_4 H)x(OC_6H_4SO_2NR^1SO_2R_f)_{(2-x)}]_n$ where x is $\leq 2$ and where $R^1$ is Na, Li, H or K, preferably Na, and where $R_f$ is any $C_1$-$C_8$ perfluoroalkyl. The haloalkoxy sulfonimide functionalized polyphosphazenes may be made by reacting $(NPCl_2)_n$, where $n \geq 3$ with $R^4$, where $R^4$ is an alkali fluoroalkoxide such as $R^1OCH_2(CF_2)_4H$, $R^1OCH_2CF_3$, $R^1OCH_2CF_2OCF_2CF_2OCF_3$, where $R^1$ is Na, Li, or K, or mixtures thereof, to displace up to about 50% of the Cl in the $(NPCl_2)_n$ to form a first reaction product, reacting the first reaction product with an alkali phenoxy sulfonimide of the formula $R^1OC_6H_4SO_2NR^1SO_2R_f$ where $R^1$ is Na, Li or K to produce a second reaction product, reacting the second reaction product with an excess of $R^4$, which again is an alkali fluoroalkoxide such as $R^1OCH_2(CF_2)_4H$, $R^1OCH_2CF_3$, $R^1OCH_2CF_2OCF_2CF_2OCF_3$, where $R^1$ is Na, Li, or K, or mixtures thereof, to produce a haloalkoxy sulfonimide functionalized polyphosphazene of the formula [$NP(R^4)x$ $(OC_6H_4SO_2NR^1SO_2R_f)_{(2-x)}]_n$ where x is $\leq 2$ and where $R^1$ is Na, Li or K, and where $R_f$ is any $C_1$-$C_8$ perfluoroalkyl.

Another aspect of the invention relates to blends of sulfonimide functionalized polyphosphazene. The blends may include a sulfonimide functionalized polyphosphazene and another polymer such as polytetrafluoroethylene (PTFE), polyvinylidene fluoride (PDVF), polyvinylidene fluoride-co-hexafluoropropylene (PVDF-HFP), polystyrene (PS), polybutadiene (BR), polyvinylidene chloride (VDC), polymethyl methacrylate (PMMA), polyvinyl alcohol (PVAL), polyvinyl acetate (PVA), polyphenylene oxide (PPO), polyether ether ketone (PEEK), polyethylene terephthalate (PET), polybutylene terephthalate (PBT), polycarbonate (PC), polyether sulfone, polybenzimidazoles (PBI), polydimethyl siloxane, polyphenylene sulfide (PS), polypyrrole, polyphenylene, polyaniline, poly(bis(pentoxy)phosphazene), poly(bis(phenoxy)phosphazene), poly((methoxyethoxyethoxy)(m-methyl phenoxy)phosphazene), styrene-acrylonitrile copolymers (SAN), acrylonitrile-butadiene-styrene terpolymers (ABS) and ethylene-methacrylic acid copolymer.

The invention also relates to a composition that includes a sulfonimide functionalized polyphosphazene polymer and an additive such as carbon black, graphite, platinum, rhuthenium, silica, montmorillonite, clay, titanium dioxide, zirconium oxide, phosphoric acid, phosphotungstic acid, silicomolybdic acid, phosphomolybdic acid, hexaphenoxycyclotriphosphazene, di(m-methylphenoxy) tetra(trifluoroethoxy)cyclotriphosphazene, cross-linkers such as peroxides, plasticizers such as water, methanol, ethanol or hexane, or lithium salts such as $CF_3SO_2NLiSO_2CF_3$.

The invention further relates to membranes of sulfonimide functionalized polyphosphazene such as of the formula [$NP(OC_6H_4SO_2NR^1SO_2R_f)_x(OC_6H_4CH_3)_{2-x}$]n where x is $\leq 2$ and where $R^1$ is Na, Li, K, or H and where $R_f$ is any $C_1$-$C_8$ perfluoroalkyl, and the use of those membranes in fuel cells.

In addition, the invention relates to manufacture of lithiated alkali phenoxy sulfonmide functionalized polyphosphazene. Manufacture entails forming a solution of a sulfonimide functionalized polyphosphazene such as [$NP(OCH_2CH_2OCH_2CH_2OCH_3)_{1.50}(OC_6H_4SO_2NHSO_2 R_f)_{0.50}$], where $R_f$ is any $C_1$-$C_8$ perfluoroalkyl, in acidic water, dialyzing the solution against LiCl solution, dialyzing against deionized water, and then against methanol, and drying the solution, concentrating the solution to produce a residue, and drying under vacuum.

DETAILED DESCRIPTION OF THE INVENTION

Materials

Trifluoromethanesulfonamide, 98+% is obtained from TCI and used as received.

4-methoxybenzenesulfonyl chloride, 99%, 4-methylphenol, 99%; 3-methylphenol, 99%, tetra(n-butyl)ammonium bromide, 99%; sodium hydride 95%; sodium methoxide, 0.5M in methanol; sodium ethanethiolate, tech., 80%; 1,4-dioxane, 99.8% (anhydrous); N,N-dimethylformamide (DMF), 99%; N,N-dimethylacetamide (DMAC), 99% and poly(vinylidene fluoride) (PVDF), Mw=530,000; are obtained from Aldrich and used as received.

Methylene chloride, chloroform, methanol, ethyl acetate (anhydrous), pentane and hydrochloric acid (36.5-38%), are obtained from EM Science and used as received.

Tetrahydrofuran (THF) is obtained from EM Science and distilled from sodium benzophenone ketyl prior to use.

Acetone is obtained from EM Science and distilled from $CaSO_4$ prior to use.

Triethylamine is obtained from Acros and distilled from $CaH_2$ prior to use.

Hexachlorocyclotriphosphazene is obtained from Ethyl Corp./Nippon Fine Chemical Co. and recrystallized from heptane and sublimed at 40° C. (0.05 mm Hg) prior to use.

Poly(dichlorophosphazene) is produced by the well known ring-opening polymerization of hexachlorocyclotriphosphazene to form poly(dichlorophosphazene) as shown in the Journal of the American Chemical Society, Vol. 87, pg. 4216 (1965). As shown therein, hexachlorocyclotriphosphazene is polymerized under vacuum for four to sixty hours at 250° C. which resulted in formation of $(NPCl_2)_n$.

Nafion 117, produced by E.I. DuPont de Nemours & Co., Inc., is obtained from Aldrich. Samples of Nafion 117 are pretreated as described in the Journal of the Electrochemical Society, Vol. 143, Issue 12 (1996).

Property Measurements

A Bruker AMX-360 spectrometer is used to obtain $^1H$ (360 MHz) and $^{31}P$ (146 MHz) NMR spectra. A Bruker AMX500 spectrometer is used to obtain $^{13}C$ (126 MHz) spectra, and a Bruker DPX-300 is used to obtain $^{19}F$ spectra (282 MHz). The $^{31}P$, $^{13}C$, and $^{19}F$ spectra are proton decoupled. The $^{31}P$ NMR spectra are referenced to external 85% $H_3PO_4$ with positive shifts recorded downfield from the reference. The $^1H$ and $^{13}C$ NMR spectra are referenced to external tetramethylsilane. The $^{19}F$ NMR spectra are referenced to external trichlorofluoromethane. All NMR spectra are obtained in $d_8$-THF with chemical shifts recorded in ppm and coupling constants recorded in Hz.

Molecular weights are determined using a Hewlett-Packard HP 1090 gel permeation chromatograph ("GPC") equipped with a HP-1047A refractive index detector. Samples are eluted with a 0.1% by weight solution of tetra (n-butyl) ammonium nitrate in THF. The GPC is calibrated with polystyrene standards (Polysciences).

Equilibrium water swelling at room temperature for the membranes is measured as the weight percent water per dry membrane weight in a fully equilibrated membrane.

Carbon, Hydrogen, Nitrogen Analysis:

Carbon, Hydrogen, Nitrogen are determined using a 2400 Perkin-Elmer CHN Elemental Analyzer. The analyzer uses combustion to convert the sample elements to $CO_2$, $H_2O$, and $N_2$. The sample, upon entering the analyzer, is combusted in a pure oxygen environment. The product gases are separated under steady state conditions, and measured as a function of thermal conductivity.

General Procedure for Synthesis of Sulfonimide Groups

The sulfonimide side groups useful for functionalization of polyphosphazenes may be produced according to Scheme A below:

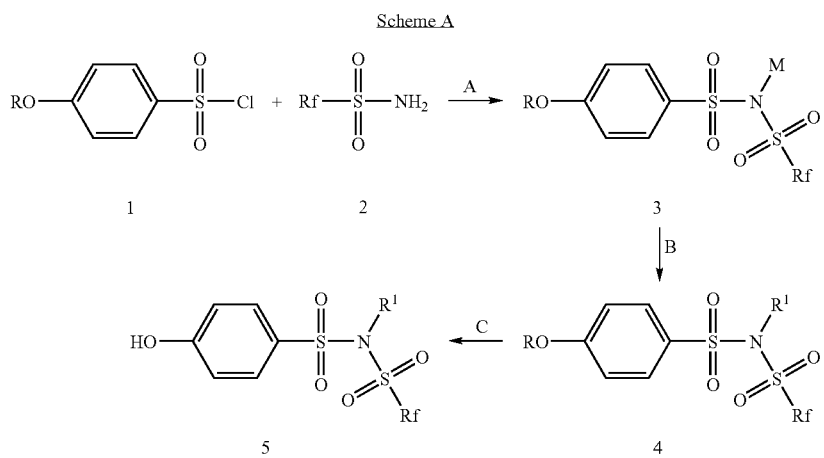

Scheme A

In Scheme A, $ROC_6H_4SO_2Cl$, where R is a $C_1$-$C_5$ alkyl, and $R_fSO_2NH_2$, where $R_f$ is any $C_1$-$C_8$ perfluoroalkyl or partially fluorinated alkyl, are reacted with a base such as Methylamine, Dimethylamine, Trimethylamine, Ethylamine, Diethylamine, Triethylamine, Pyridine, Imidazole, Pyrimidine or mixtures thereof in the presence of a solvent such as Acetone, Acetonitrile, N,N-dimethylacetamide, N,N-dimethylformamide, Dimethyl sulfoxide, Hexamethylphosphoramide, Nitromethane, Pyridine, Tetrahydrofuran or mixtures thereof. The reaction may proceed at about 25° C. to about 60° C. for about 1 hour to about 72 hours to produce intermediate 3 where M is any of H, Li, K, Na, $R'_3NH+$ where R' is $C_1$-$C_5$ alkyl, or mixtures thereof. Intermediate 3 then is reacted with an alkali metal salt such as Lithium methoxide, Lithium ethoxide, Lithium tert-butoxide, Lithium phenolate, Lithium hydroxide, Sodium methoxide, Sodium ethoxide, Sodium tert-butoxide, Sodium phenolate, Sodium hydroxide Potassium methoxide, Potassium ethoxide, Potassium phenolate, Potassium tert-butoxide, Potassium hydroxide or mixtures thereof in the presence of a solvent such as Methanol, Ethanol, Isopropanol, tert-Butanol, Acetone, Acetonitrile, N,N-dimethylacetamide, N,N-dimethylformamide, Dimethyl sulfoxide, Hexamethylphosphoramide, Nitromethane, Tetrahydrofuran or mixtures thereof for about 0.2 hours to about 24 hours at about 25° C. to about 60° C. give intermediate 4 where $R^1$ is any of Li, K or Na. Intermediate 4 then may be treated according to any of the following routes (a)-(u) to yield upon work-up the sulfonimide end product 5:

a. React intermediate 4 with Trimethylsilyl iodide in Chloroform at about 25° C. to about 50° C., for about 12 to about 140 hrs.
b. React intermediate 4 with Sodium ethane thiolate in N,N-dimethylformamide at Reflux, about 3 hrs
c. React intermediate 4 with Sodium sulfide in N-methylpyrrolidone at about 140° C., for about 2 to about 4 hrs
d. React intermediate 4 with Lithium diphenyl phosphide and HCl, Water in THF at about 25° C., about 2 hrs t. React intermediate 4 with Silicon tetrachloride and Sodium iodide in Dichloromethane, acetonitrile for about 14 hrs
u. React intermediate 4 with Trifluoromethane sulfonic acid at about −5° C., about 60 secs General Procedure for Synthesis of $NaOC_6H_4SO_2NNaSO_2CF_3$ Synthesis of the sulfonimide side group $NaOC_6H_4SO_2NNaSO_2CF_3$ is outlined in scheme 1 below.

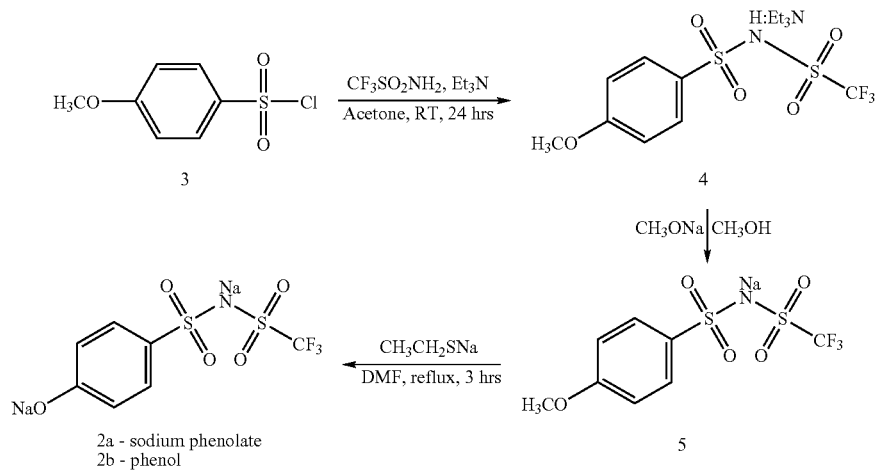

Scheme 1 e. React intermediate 4 with Sodium cyanide in Dimethyl sulfoxide at about 125° C. to about 180° C., about 5 to about 48 hrs
f. React intermediate 4 with Lithium iodide in Collidine at Reflux, about 10 hrs
g. React intermediate 4 with Aluminum bromide in Ethane thiol at about 25° C., about 1 hr
h. React intermediate 4 with Boron tribromide in Dichloromethane at about −80° C. to about −20° C., about 12 hrs
i. React intermediate 4 with Tribromo(dimethyl sulfide) boron in 1,2-Dichloroethane at about 83° C.
j. React intermediate 4 with 9-Bromo-9-borabicyclo(3.3.0) nonane in Dichloromethane at Reflux
k. React intermediate 4 with 2-Bromo-1,3,2-benzodioxaborole and Boron trifluoride diethyletherate in Dichloromethane at about 25° C., about 0.5 to about 36 hrs
l. React intermediate 4 with Pyridine hydrochloride at about 220° C., about 6 mins
m. React intermediate 4 with Methyl magnesium iodide at about 155° C. to about 165° C., about 15 mins
n. React intermediate 4 with Hydrobromic acid in Acetic acid at Reflux, about 30 mins
o. React intermediate 4 with Boron trichloride in Dichloromethane at about −20° C.
p. React intermediate 4 with Aluminum chloride at about 0° C., about 3 hrs
q. React intermediate 4 with Lithium chloride in N,N-dimethylformamide at about 4 to about 72 hrs
r. React intermediate 4 with Trifluoromethane sulfonic acid and Methyl phenyl sulfide at about 0° C. to about 25° C.
s. React intermediate 4 with Titanium tetrachloride in Dichloromethane at about 0° C.

The sulfonimide $NaOC_6H_4SO_2NNaSO_2CF_3$ is unique in that the sulfonimide functionality is essentially non-nucleophillic. This enables use of $NaOC_6H_4SO_2NNaSO_2CF_3$ in macromolecular chlorine replacement of a poly(dichlorophosphazene) and to tailor the phosphazene polymer through choice of cosubstituents with $NaOC_6H_4SO_2NNaSO_2CF_3$.

Synthesis of Amine Terminated Sulfonimide

Sulfonimides for use in the invention also may be amine functionalized. Amine terminated sulfonimides of the formula $H_2NC_6H_4SO_2NR^1SO_2R_f$, where $R^1$ is any of Li, K or Na, and where $R_f$ is any $C_1$-$C_8$ perfluoroalkyl, such as $H_2NC_6H_4SO_2NR^1SO_2CF_3$, where $R_f$ is —$CF_3$, may be prepared according to scheme 1A.

Scheme 1A

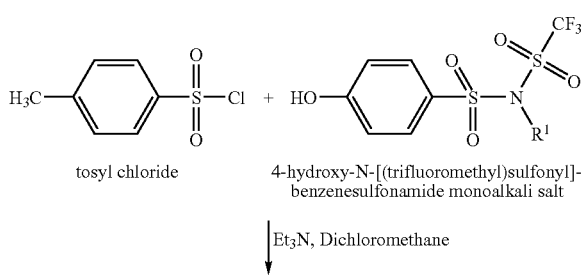

tosyl chloride     4-hydroxy-N-[(trifluoromethyl)sulfonyl]-benzenesulfonamide monoalkali salt Et₃N, Dichloromethane

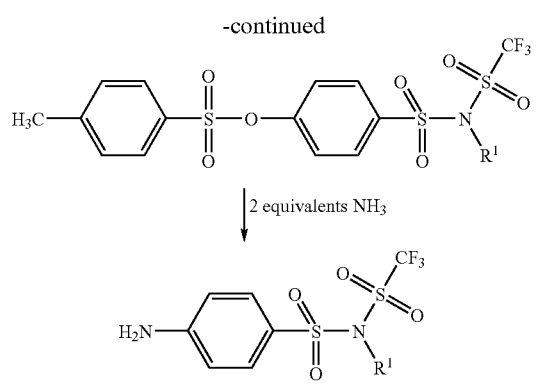

4-amino-N-[(trifluoromethyl)sulfonyl]-benzenesulfonamide monoalkali salt

The hydroxyl termination of the sulfonimide species may be converted to an amine to produce an amine linkage to the polyphosphazene backbone to provide another option for connectivity. To illustrate, one equivalent of the phenolic form of an alkali sulfonimide derivative such as $HOC_6H_4SO_2NR^1SO_2CF_3$ where $R^1$ is any of Li, K or Na and one equivalent of tosyl chloride is dissolved in dichloromethane in sufficient volume to solubilize the reagents to a desired concentration. One equivalent of a base such as triethylamine is dripped into the stirring reaction mixture. As the reaction continues, triethylamine hydrochloride salt precipitates out of solution. Reaction progress may be monitored by thin layer chromatography, and upon completion the triethylamine hydrochloride salt may be filtered out of the solution. To the filtered solution, two equivalents of $NH_3$ are slowly added. The resulting amine terminated sulfonimide product may be isolated through liquid extraction.

General Procedures for Synthesis of Phenoxy Sulfonimide Functionalized Polyphosphazene Polymer Synthesis of alkali phenoxy sulfonimide functionalized polymers such as $—OC_6H_4SO_2NNaSO_2CF_3$ functionalized polyphosphazene polymers may be accomplished by several alternative methods. These methods include sequential addition of reactants as shown in Scheme B; simultaneous addition of the first and second salts used in scheme B is shown in scheme BB, and simultaneous addition of all three salts used in scheme B is shown in scheme BC.

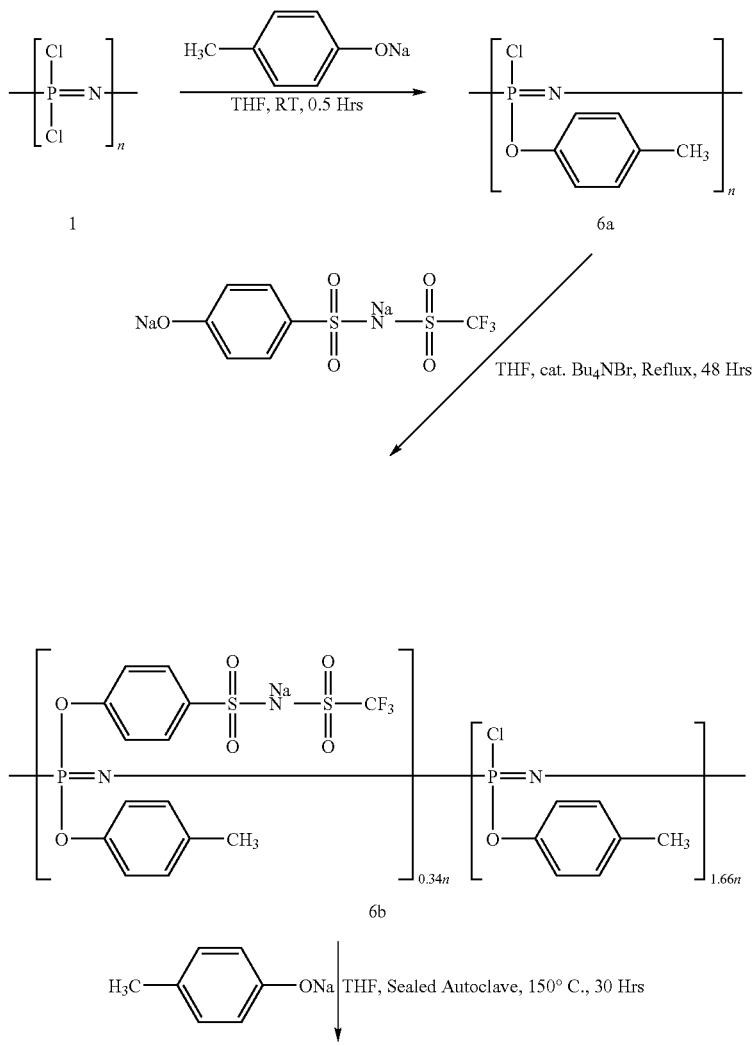

Scheme B

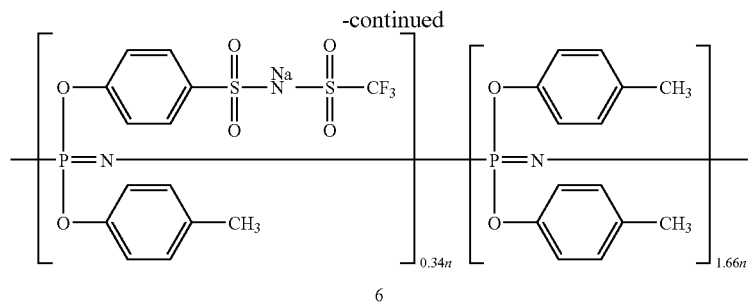

6

In Scheme B, poly(dichloro)phosphazene 1 where n=3 or more is first substituted with about 0.5 equivalents of an alkali oxide derivative such as sodium p-methyl phenoxide, lithium p-methyl phenoxide, potassium p-methyl phenoxide, or any combination thereof to produce intermediate 6a. The alkali oxide derivative may be added prior to or simultaneous with addition of a second alkali salt such as $NaOC_6H_4SO_2NNaSO_2CF_3$, $LiOC_6H_4SO_2NNaSO_2CF_3$, $KOC_6H_4SO_2NNaSO_2CF_3$ or mixtures thereof. Addition of the second alkali salt may be performed with or without a phase transfer agent such as tetrabutyl ammonium bromide, preferably in the presence of a phase transfer agent. Refluxing follows addition of the reagents, and proceeds until completion of addition of the second alkali salt, usually over a period of about 24 hours to about 48 hours to produce intermediate 6b. A third alkali salt such as $H_3CC_6H_4ONa$, $NaOC_6H_5$, $NaOC_6H_4CF_3$, $H_3CC_6H_4OLi$, $LiOC_6H_5$, $LiOC_6H_4CF_3$, $H_3CC_6H_4OK$, $KOC_6H_5$, $KOC_6H_4CF_3$ or mixtures thereof then may be added, placed into an autoclave (high temperature/high pressure reactor), and heated under elevated temperature and pressure, such as to 150° C., 3.5-4 Bar pressure. Alternatively, addition of the third alkali salt may be done outside of an autoclave under reflux conditions until the substitution is complete as determined by $^{31}P$ NMR. In this alternative, the solvent may be changed to dioxane to achieve a higher reflux temperature to promote more effective substitution. Additionally, if the first or third or any subsequent number of salts which are added are non-sterically hindered, such as linear alkoxy salts such as $NaOCH_2CF_3$ or $NaOCH_2CH_2OCH_2CH_2OCH_3$, then the conditions required for complete substitution are less harsh and benchtop substitutions may proceed without the need of an autoclave.

In scheme BB, refluxing follows addition of the initial two or more reagents and proceeds through completion, usually about 24-48 hours. The third salt employed in scheme B then may be added in an autoclave, and then heated to an elevated temperature and pressure, such as, about 150° C. and about 3.5-4 bar. Here $R^1$ represents any alkali such as Na, K, or Li, or mixtures thereof.

Scheme BB

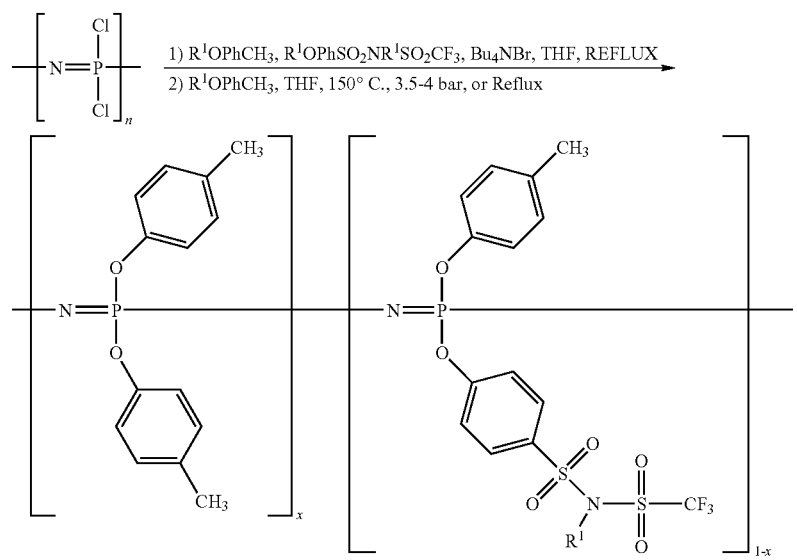

In scheme BC, all three salts employed in scheme B are added simultaneously. The total equivalents of the combined salts employed do not exceed the total number of chlorine equivalents, or may employ an excess, keeping the total number of equivalents of combined salts so as to maintain a desired ratio between the nucleophile equivalents and the number of equivalents desired to be attached to the polymer upon completion of the reaction, accounting for the reactivity rates, steric hinderences, and displacement behaviors of the substituents. In Scheme BC, $R^1$ represents an alkali such as Na, K, or Li, or mixtures thereof.

Scheme BC

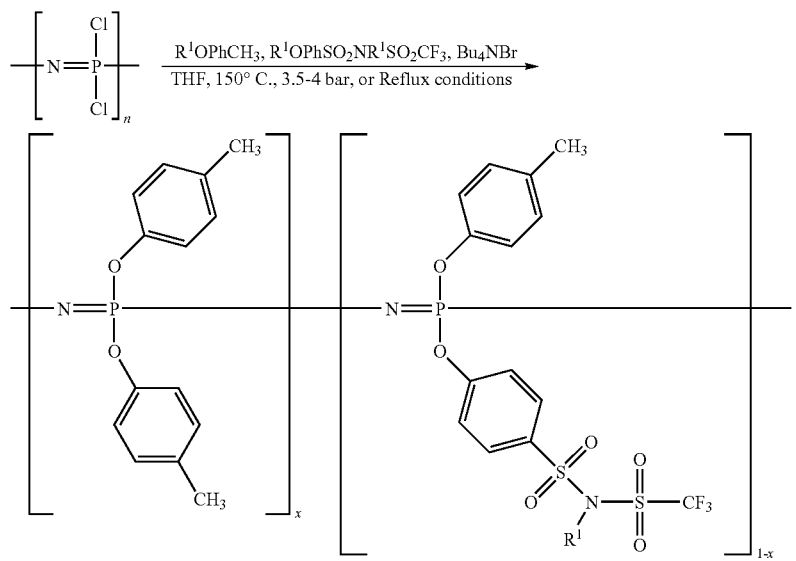

Synthesis of the Sulfonimide Functionalized Polyphosphazene Polymer 6.

As shown in scheme B, poly(dichlorophosphazene) 1 where n=3 or more is treated with an alkali alkyl phenoxide such as sodium 4-methylphenoxide to displace about 50% of the chlorine atoms on the polyphosphazene to produce intermediate polymer 6a. A suspension of an alkali sulfonimide such as $NaOC_6H_4SO_2NaSO_2CF_3$ in a solvent such as THF with tetrabutylammonium bromide as a phase-transfer agent is made by reaction of the phenol form of the sulfonimide with a suspension of NaH and tetrabutyl ammonium bromide in distilled THF. The suspension is added to polymer 6a to produce a reaction mixture which is refluxed for about 48 hours to produce intermediate polymer 6b. The remaining chlorine atoms in polymer 6b are displaced by treatment of polymer 6b with an alkali alkyl phenoxide such as sodium 4-methylphenoxide in a sealed autoclave at an elevated temperature such as about 100° C. to about 200° C., typically about 150° C. for about 12 hours to about 40 hours, typically about 30 hours, at a pressure of about 1.5 bar to 12 about bar, typically about 3.5 to 4.0 bar to yield polymer 6 end product. The sulfonimide groups are then converted to their acid form by multiple precipitations of the polymer solution into concentrated HCl, or by the addition of HCl to the polymer solution. Purification of the functionalized polymer is performed by dialysis and precipitation into pentane, or through a multiple precipitation process to give purified polymer 6.

The synthesis of polyphosphazenes bearing a sulfonimide functionality is not limited to traditional linear architectures. Low numbers of repeat units in the polydichlorophosphazene chain may be used to produce oligomers or cyclic species. For these low molecular weight derivatives, the synthesis may follow the same pathway (n=3 in structure 1, Scheme B).

Additionally, sulfonimide polyphosphazenes may subsequently be further functionalized and/or reacted with other polymeric, polymerizable, or small molecule species such as but not limited to diols such as ethylene glycol, diamines such as diaminoheptane, or end functionalized polymers or oligomers such as end functionalized polystyrene, to provide branched, grafted, pendent, cross-linked, cyclolinear, or co-polymer species.

In another embodiment, the substituents may be solely the sulfonimide derivative so as to yield sulfonimide functionalized polyphosphazene homopolymer as in scheme B1, whereas Scheme B2 produces a sulfonimide functionalized polyphosphazene copolymer which has a cosubstituent.

Synthesis of Polyphosphazene Homopolymer

In Scheme B1, a polyphosphazene where n=3 or more is reacted with $R^1OPhSO_2NNaSO_2CF_3$, where $R^1$ is an alkali metal such as Na, Li, K or mixtures thereof to produce a phosphazene homopolymer functionalized by a sulfonimide derivative. In this embodiment, the sulfonimide is formed as above, using an alkali metal oxide. The reaction may be performed with or without a phase transfer agent, preferably with a phase transfer agent. The reaction may proceed in an autoclave at about 60° C. to about 240° C., such as about 150° C., and at about 3.5-4 Bar for about 12 hours to about 40 hours, or under reflux conditions at atmospheric pressure. Purification of the resulting homopolymer may be performed as above. Alternatively, the homopolymer may be formed through the use of the amine terminated sulfonimide species. In this aspect, $NH_2C_6H_4SO_2NR^1SO_2CF_3$ is used as the nucleophile in place of $R^1OC_6H_4SO_2NR^1SO_2CF_3$. In this aspect, the reaction proceeds as for the nucleophile $R^1OC_6H_4SO_2NR^1SO_2CF_3$ except that an additional equivalent of a base such as triethylamine or pyridine must be added.

Scheme B1

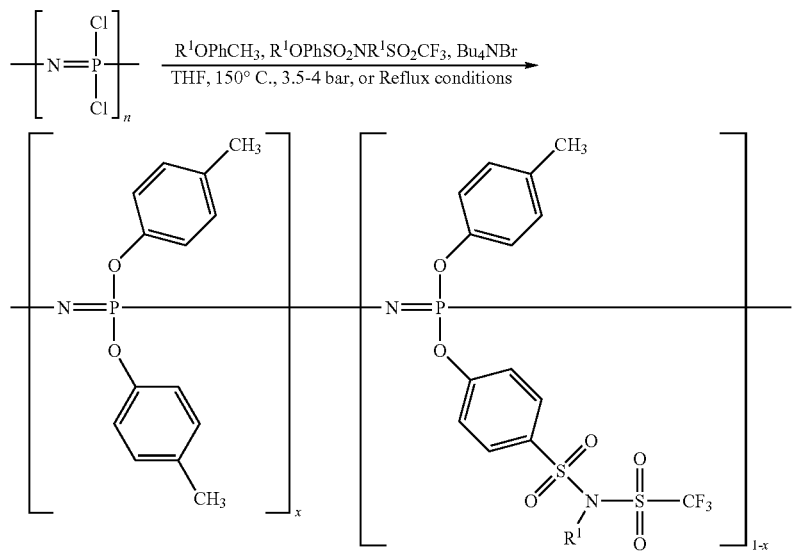

Synthesis of Polyphosphazene Copolymer

In Scheme B2, a polyphosphazene where n=3 or more is reacted with the sulfonimide functionality and one or more differing nucleophiles bearing an alkali oxide or amine linkage site, here represented by $R^3R^2$, to produce a phosphazene copolymer functionalized by a sulfonimide derivative and cosubstituent. $R^3$ is an alkali metal oxide such as NaO—, LiO—, KO— or mixtures thereof, or an amine such as $NH_2$—. $R^2$ refers to a co-substituent or co-substituent precursor which may be, but is not limited to, an alkyl such as —$CH_2CH_3$, an aryl such as —$C_6H_4CH_3$, an alkyl ether such as —$CH_2CH_2OCH_2CH_2OCH_3$, a functionalized alkyl or functionalized alkyl precursor such as —$CH_2CH_2OTHP$ where THP is tetrahydropyranyl moiety, a functionalized aryl or functionalized aryl precursor such as —$C_6H_4COOPr$, a fluoroalkyl such as —$CH_2CF_3$, a fluoroalkyl ether such as —$CH_2CF_2OCF_2CF_2OCF_3$, aryl such as $C_6H_4CF_3$ or —$C_6F_5$, or combination thereof. Z is O when the sulfonimide moiety is linked through an alkali oxide linkage; Z is NH where the amine form of the sulfonimide moiety is used. The $Bu_4NBr$ is used in the reaction if the substituents are bulky or sterically hindered. The $NEt_3$ (or other base) is use when amine linkages are desired. In scheme B2, the ratio of the compounds $(R^3R^2):(R^3C_6H_4SO_2NR^1SO_2CF_3)$ where $R^1$ is Li, K, or Na, may vary over a wide range, such as about 1:0.001 to about 0.001:1.

Scheme B2

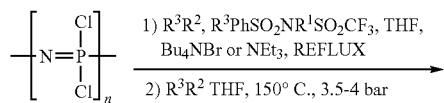

-continued

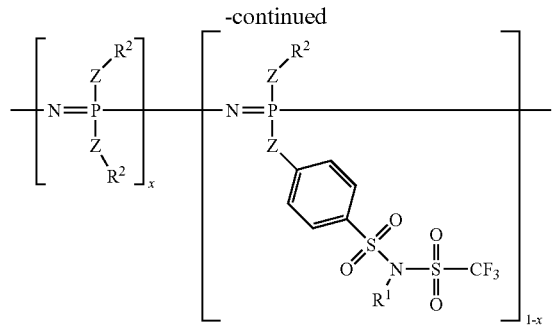

Typically, the cosubstituent represented by $R^2$ is a non-sulfonimide derivative chosen to produce a desired property in the final polyphosphazene copolymer. The amount of sulfonimide and cosubstituent preferably are such as to substitute to 100 percent of the available sites for substitution. In instances where the cosubstituent is likely to cause steric hinderance, an extra amount of the cosubstituent, such as about 0.01 equivalents to about 0.5 equivalents of the cosubstituent may be added to ensure complete substitution. If a combination of cosubstituents is used and where all of which may generate steric hinderance, useful ratios of cosubstituents may be obtained through sequential addition of the cosubstituent neucleophiles while taking into account reactivity and displacement behaviors. Extra equivalents of the final cosubstituent or simultaneous addition of cosubstituents which have similar reactivity while using an equal excess of each cosubstituent may be done. Where the co-substituents are not sterically hindered, addition of the cosubstituent typically does not require excess amounts of cosubstituents. Typically, the number of equivalents remains at one per available substitution site.

Acidification may be achieved by dissolving the polymer in a lower alkyl alcohol such as methanol or isopropanol and then precipitating the polymer multiple times into concentrated HCl or dilute HCl, followed by further purification via dialysis or precipitation into pentane, heptane, or hexane.

Alternatively, the acidification may be achieved by dissolving the polymer in a lower alkyl alcohol such as methanol or isopropanol and then slowly adding aliquots of concentrated HCl to the stirring solution over a period of several hours. Concentrated HCl then is added to precipitate the polymer from the solution, followed by further purification via dialysis or precipitation into pentane, heptane or hexane.

Synthesis of a Haloalkoxy Sulfonimide Functionalized Polymer

Synthesis of a haloalkoxy co-substituted polymer is outlined in Scheme 3 below. Scheme 3:

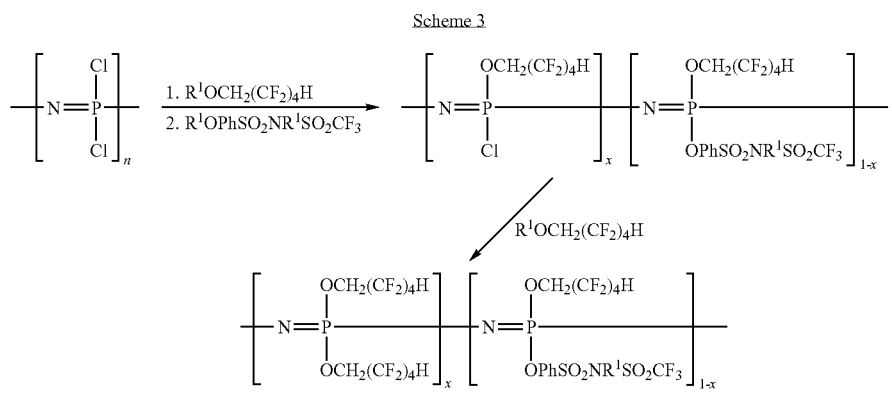

As shown in scheme 3, poly(dichlorophosphazene) is treated with a solution of alkali fluoroalkoxide such as NaOCH$_2$(CF$_2$)$_4$H, NaOCH$_2$CF$_3$, NaOCH$_2$CF$_2$OCF$_2$CF$_2$OCF$_3$LiOCH$_2$(CF$_2$)$_4$H, LiOCH$_2$CF$_3$, LiOCH$_2$CF$_2$OCF$_2$CF$_2$OCF$_3$, KOCH$_2$(CF$_2$)$_4$H, KOCH$_2$CF$_3$, KOCH$_2$CF$_2$OCF$_2$CF$_2$OCF$_3$ or mixtures thereof in a solvent such as THF, dioxane, toluene or mixtures thereof to displace about 50% of the chlorine atoms of the poly(dichlorophosphazene) and to form a reaction mixture. Then, a suspension formed of an alkali phenoxy sulfonimide such as R$^1$OC$_6$H$_4$SO$_2$NR$^1$SO$_2$CF$_3$, where R$^1$ is Li, Na, K, or a combination thereof, in a solvent such as THF, dioxane, toluene or mixtures thereof is added to the reaction mixture and stirred at room temperature to produce the partially substituted polymer intermediate. Remaining chlorine atoms are displaced by treatment of the intermediate with excess alkali fluoroalkoxide such as NaOCH$_2$(CF$_2$)$_4$H, NaOCH$_2$CF$_3$, NaOCH$_2$CF$_2$OCF$_2$CF$_2$OCF$_3$ LiOCH$_2$(CF$_2$)$_4$H, LiOCH$_2$CF$_3$, LiOCH$_2$CF$_2$OCF$_2$CF$_2$OCF$_3$, KOCH$_2$(CF$_2$)$_4$H, KOCH$_2$CF$_3$, KOCH$_2$CF$_2$OCF$_2$CF$_2$OCF$_3$ or mixtures thereof. The reaction mixture then is concentrated to generate a viscous liquid. The viscous liquid is precipitated into concentrated acid such as HCl and dialyzed against a blend of lower alkyl alcohols such as (methanol/isopropanol), (ethanol/isopropanol), or (methanol/ethanol). The dialyzed solution is concentrated again and precipitated into concentrated acid such as HCl, and then air dried. The polymer then is further acidified from a lower alkyl alcohol such as methanol or ethanol and then washed, collected and dried.

Sulfonimide Functionalized Polyphosphazene in Silicate Matrix

In another embodiment, a polyphosphazene that has been functionalized with sulfonimide substituents is provided in a silicate matrix by use of the sol-gel process.

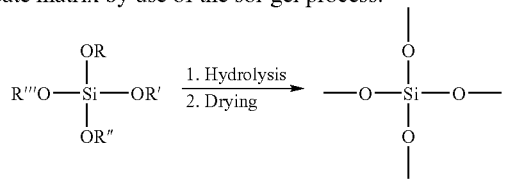

-continued

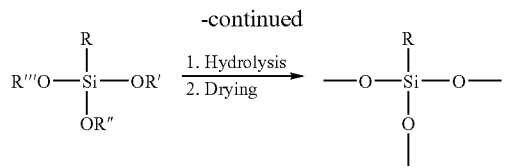

In this embodiment, a polyphosphazene that has been functionalized with a sulfonimide substituent is solvated into a reaction solvent such as Methanol, Ethanol, Isopropanol, tert-Butanol, Acetone, Acetonitrile, N,N-dimethylacetamide, N,N-dimethylformamide, Dimethyl sulfoxide, Hexamethylphosphoramide, Nitromethane, Tetrahydrofuran or mixtures thereof. Typically, the amount of functionalized polyphosphazene polymer is about 1 wt. % to about 50 wt % of the solvated end product. The remaining 1-50% of the end product is an orthosilicate species. Possible hydrolysis conditions include but are not limited to 0.0001M-1 M HCl, 0.0001M-1 M HBr, 0.0001M-1 M HI, 0.0001M-1 M LiOH, 0.0001M-1 M NaOH, or 0.0001M-1 M KOH. The reaction occurs between the orthosilicate units, wherein R, R', R" may be the same or different and which may be an alkyl such as methyl, ethyl, or propyl, a fluoroalkyl such as trifluoromethyl, a trifluoroethyl, aryl such as a phenyl, or a fluoroaryl such as fluorobenzene.

Blends of Functionalized Polyphosphazene Polymer

The functionalized polyphosphazenes may be blended, laminated, electrospun, grafted, co-polymerized, or formed into interpenetrating networks (IPNs) or Semi-IPNs (partial IPNs). The functionalized polyphosphazenes may be blended with other functionalized or non-functionalized, linear, block, graft, comb, branched, cross-linked, or non-cross-linked polymers such as polytetrafluoroethylene (PTFE); fluorinated hydrocarbons such as polyvinylidene fluoride (PDVF), and copolymers of PVDF such as polyvinylidene fluoride-co-hexafluoropropylene (PVDF-HFP), and olefins such as polystyrene (PS), polybutadiene (BR), polyvinylidene chloride (VDC); Acrylics such as polymethyl methacrylate (PMMA); Polyvinyls such as: polyvinyl alcohol (PVAL), polyvinyl acetate (PVA); polyurethanes such as flexible, rigid, or elastomeric polyurethanes; polyethers such as polyacetal, polyphenylene oxide (PPO), polyether ether ketone (PEEK); polyesters such as polyethylene terephthalate (PET), polybutylene terephthalate (PBT), polycarbonate (PC); polyamides and polyimides such as nylons; Polysulfones such as polyether sulfone; Polyimidazoles such as polybenzimidazoles (PBI); Silicone polymers such as polydimethyl siloxane; heteroatom polymers such as polyphenylene sulfide (PS), polypyrrole; aromatic or cyclic polymers such as polyphenylene and polyaniline; and other polyphosphazes such as poly(bis(pentoxy)phosphazene) and poly(bis(phenoxy)phosphazene); and copolymers of any of the above, such as poly((methoxyethoxyethoxy)(m-methyl phenoxy) phosphazene), styrene-acrylonitrile copolymers (SAN), Acrylonitrile-butadiene-styrene terpolymers (ABS) and ethylene-methacrylic acid copolymers.

Polymers containing a sulfonimide functionality also may be blended or compounded with additives such as Carbons such as carbon fillers, carbon black, graphite; metals such as platinum, rhuthenium; silicates and clays such as silica, montmorillonite, clay; metal oxides such as titanium dioxide and zirconium oxide; acids such as phosphoric acid; heteropolyacids such as phosphotungstic acid, silicomolybdic acid and phosphomolybdic acid; ion exchanged forms of the above using alkali ions such as cesium, sodium, lithium, or alkaline earth metal ions such as calcium, magnesium, or mixtures thereof. Small molecule functional units such as phosphazene cyclic trimers, homo and hetero substituted, such as hexaphenoxycyclotriphosphazene, di(m-methylphenoxy)tetra(trifluoroethoxy)cyclotriphosphazene. Cross-linkable additives such as peroxides, difunctional or multifunctional small molecules. Plasticizers such as water, methanol, ethanol, hexanes, other solvents or small molecule plasticizers, and lithium salts such as $CF_3SO_2NLiSO_2CF_3$.

Sulfonimide functionalized polyphosphazene polymers may be cross-linked through gamma radiation, UV radiation, thermal, ionic, free-radical, or additive types of methods, depending upon the choice of co-substituent present with the sulfonimide moiety or the choice of additive present within the system, or the choice of copolymer or blended polymer present. The polymers may be processed by various techniques such as solution casting, spin casting, hot pressing, molding, electrospinning, extrusion.

Membranes

The functionalized phosphazene polymers may be cast into membranes. The membranes may be cast from solvents such as tetrahydrofuran, dimethyl formamide, dimethyl acetamide, 1,4-dioxane or mixtures thereof, preferably dimethylacetamide. Casting of membranes of the functionalized phosphazene polymers, as well as blends of the functionalized phosphazene polymers entails dissolution of the polymer in a high boiling solvent such as DMF or DMAC over a wide range of concentrations, followed by drying in a vacuum oven under reduced pressure, typically for about 24 hours at room temperature, and then at reduced pressure at elevated temperatures of about 30° C. to 70° C. for about 24 to 72 hours, such as about 60° C. for about 60 hours.

Lithiated Sulfonimide Functionalized Polyphosphazenes

Any of the aforementioned polyphosphazenes bearing the sulfonimide substituent, preferably bearing at least some portion of an oligo-oxy type co-substituent such as methoxyethoxyethoxy substituent, may be applied to a lithium battery application. This is accomplished through ion exchange process in which a sulfonimide functionalized polymer synthesized as described in any of the previous embodiments is dialyzed against LiCl solution to convert the polymer to a lithiated form. Further purification is accomplished through dialysis against deionized water.

To illustrate, a lithiated phenoxy sulfonimide functionalized polyphosphazene such as $[NP(OR^5)_x(OC_6H_4SO_2NLiSO_2R_f)_{2-x}]_n$, where x is $\leq 2$ and where $R_f$ is a $C_1$-$C_8$ perfluoroalkyl and where $R^5$ is an oligo-oxy substituent such as $CH_2CH_2OCH_2CH_2OCH_3$, $-CH_2CF_2OCF_2CF_2OCF_3$, $-CH_2CH_2OCH_2CH_2OCH_2CH_2OCH_3$ may be made by forming an aqueous, acidic solution of $[NP(OR^5)_x(OC_6H_4SO_2NHSO_2R_f)_{2-x}]_n$ where x is $\leq 2$ and subjecting the solution to dialysis against a LiCl solution. In one aspect, $R^5$ is $-OCH_2CH_2OCH_2CH_2OCH_3$ and the polyphosphazene has the formula $[NP(OCH_2CH_2OCH_2CH_2OCH_3)_x(OC_6H_4SO_2NLiSO_2R_f)_{2-x}]_n$ where x is $\leq 2$ and where $R_f$ is a $C_1$-$C_8$ perfluoroalkyl.

The invention will now be discussed by reference to the following non-limiting examples.

Example 1

Synthesis of Sodium Bearing Phenolic Compound $NaOC_6H_4SO_2NNaSO_2CF_3$

Triethylamine (40.0 mL, 0.29 mol) is added via syringe to a solution of 4-methoxybenzenesulfonyl chloride (25.0 g, 0.12 mol) and trifluoromethanesulfonamide (20 g, 0.13 mol) in 250 mL freshly distilled acetone and stirred at room temperature for 48 hours. The resulting solution is concentrated by reduced pressure rotary evaporation by using a Buchi Rotavapor rotary evaporator. The evaporator, at an RPM setting of 280, is set up with a water aspirator to generate reduced pressure. The evaporation produced a residue, to all of which is added 250 mL 1.0 M HCl. The resulting solution is extracted with three 250 mL portions of methylene chloride. The extracts are combined and then dried over anhydrous sodium sulfate. The methylene chloride solvent is removed by reduced pressure rotary evaporation by using the Buchi Rotavaporator as described above, followed by drying at 0.1 mmHg for 72 hours to give 31 g of the intermediate triethylammonium salt $H_3COC_6H_4NH(N(C_2H_5)_3)$ $SO_2CF_3$. The $H_3COC_6H_4NH(N(C_2H_5)_3)$ $SO_2CF_3$ is analyzed and found to have the following properties:

$^1$H NMR ($\delta$, $d_8$-THF) 1.23 (t, 9H, $CH_3$), 3.15 (q, 6H, $CH_2$), 3.70 (s, 3H, $CH_3O$), 6.83 (d, 2H, aromatic), 7.71 (d, 2H, aromatic), 8.10 (s, $^1$H, NH).

31 g of the $H_3COC_6H_4NH(N(C_2H_5)_3)SO_2CF_3$ then is dissolved in 150 mL methanol to produce a solution to which is added a solution of 148 mL of 0.5M sodium methoxide in methanol. The resulting combined solution is stirred for 20 minutes and then evaporated by reduced pressure rotary evaporation by using the Buchi Rotavapor as described above to produce a tan solid, all of which is dissolved in 100 mL methanol, whereafter the methanol is evaporated via reduced pressure rotary evaporation by using the Buchi Rotavapor as described above, followed by drying at 0.1 mm Hg for 72 hours to give sodium salt 5 of the formula $H_3COC_6H_4NNaSO_2CF_3$, all of which is dissolved in 800 mL DMF and then sodium ethanethiolate, 80% purity, (30.0 g, 0.29 mol) is added to produce a reaction mixture. The reaction mixture is refluxed at 153° C. for three hours, after which bulk DMF is removed from the mixture by vacuum distillation to yield a residue of $NaOC_6H_4SO_2NNaSO_2CF_3$. The residue of $NaOC_6H_4SO_2NNaSO_2CF_3$ is further concentrated under vacuum at 35° C. for 48 hours. All of the concentrated residue of $NaOC_6H_4SO_2NNaSO_2CF_3$ then is dissolved in 250 mL distilled water to form a solution. Then, 250 mL saturated aqueous sodium chloride solution is added to produce an aqueous solution that is extracted with two 500 mL portions THF that are then discarded. The resulting aqueous solution is then treated with 25 mL concentrated HCl to pH 3 to convert $NaOC_6H_4SO_2NNaSO_2CF_3$ to $HOC_6H_4SO_2NNaSO_2CF_3$ and then extracted with three 250 mL portions THF. The extracts are dried over anhydrous sodium sulfate and concentrated by reduced pressure rotary evaporation by using the Buchi Rotavapor as described above to produce a residue of $HOC_6H_4SO_2NNaSO_2CF_3$.

All of the $HOC_6H_4SO_2NNaSO_2CF_3$ is dissolved in 80 ml ethyl acetate to produce a solution that is filtered to remove insoluble products. Final purification of $HOC_6H_4SO_2NNaSO_2CF_3$ is done by precipitating it as a fine white powder from the ethyl acetate by addition of chloroform. The $HOC_6H_4SO_2NNaSO_2CF_3$ is then collected via filtration and dried at 0.1 mm Hg for a period of 7 days at 65° C. to give 28.2 g of $HOC_6H_4SO_2NNaSO_2CF_3$. The $H_3COC_6H_4NNaSO_2CF_3$ compound is analyzed and found to have the following properties:

$^1$H NMR ($\delta$, $d_8$-THF) 6.78 (d, 2H, aromatic), 7.74 (d, 2H, aromatic), 8.87 (s, 1H, phenol proton). $^{19}$F NMR ($\delta$, $d_8$-THF) −81.32 (s, $CF_3$). $^{13}$C NMR ($\delta$, $d_8$-THF) 114.7 (aromatic), 120.8 (q, $^1J_{CF}$ 323 Hz, $CF_3$), 128.5 (aromatic), 136.1 (aromatic-S), 160.7 (aromatic-O). MS (ESI) m/e 304 (M-1).

Example 2

Synthesis of $NaOC_6H_4SO_2NNaSO_2CF_3$ Functionalized Polyphosphazene Polymer 6

4-methylphenol (3.73 g, 0.035 mol) is dissolved in 10 mL THF and added dropwise to a suspension of sodium hydride (0.83 g, 0.035 mol) in 60 mL THF to produce sodium 4-methyl phenoxide. $HOC_6H_4SO_2NNaSO_2CF_3$ (4.06 g, 0.012 mol) is dissolved in 50 mL THF and added dropwise to a suspension of sodium hydride (0.30 g, 0.012 mol) and tetra (n-butyl)ammonium bromide (0.4 g) in 50 mL THF and stirred for 16 hours to produce a sodium phenoxide solution of the sulfonimide $NaOC_6H_4SO_2NNaSO_2CF_3$.

All of the sodium 4-methylphenoxide then is added dropwise to a stirring polymeric solution of poly(dichlorophosphazene) 1 (4.0 g, 0.035 mol) in 400 mL THF and stirred for 30 minutes to yield a partially substituted polyphosphazene polymer. The $NaOC_6H_4SO_2NNaSO_2CF_3$ is then added dropwise to this partially substituted polymer solution and then heated to reflux at 67° C. for 48 hours, and cooled to room temperature. The cooled polymeric solution, in an amount of 570 ml, then is transferred to an autoclave.

4-methylphenol (7.45 g, 0.069 mol) is dissolved in 10 mL THF to form a solution. All of this solution then is added dropwise to a suspension of sodium hydride (1.57 g, 0.065 mol) in 40 mL THF to form a sodium 4-methylphenoxide solution. All of the sodium 4-methylphenoxide solution then is added to the polymeric solution in the autoclave. The autoclave is sealed and heated to 150° C. to generate a pressure of 3.5 bar. After 30 hours, the autoclave is cooled to room temperature and the resulting product of substituted polymer in solution is concentrated via rotary evaporation by using the Buchi Rotavapor as described above, until viscous. Then, all of the viscous polymer solution is precipitated into 6 M aqueous HCl and the polymer precipitate allowed to air dry in a fume hood.

The resulting dried polymer is dissolved in dioxane and then precipitated into concentrated HCl to form a precipitate of polymer that is air dried at room temperature. This step is repeated twice for a total of three precipitations. After the third precipitation, the polymer is placed in distilled water and soaked for 16 hours. The soaked polymer then is dried under vacuum for 24 hours. Then, all of the resulting dried polymer is dissolved in 200 ml of a 50/50 (v/v) blend of 1,4-dioxane/methanol. The resulting solution is placed in 12-14K dialysis tubing, and dialyzed against a 50/50 (v/v) dialysis solution of 1,4-dioxane/methanol. At 24 hours the dialysis solution is changed to 75/25 (v/v) 1,4-dioxane/methanol. At 48 hours the dialysis solution is changed to 1,4-dioxane, and at 72 hours the dialysis solution is changed to fresh 1,4-dioxane. The resulting, dialyzed polymer solution is vacuum filtered and concentrated via reduced pressure rotary evaporation by using the Buchi Rotavapor as described above, until viscous. The resulting, viscous polymer then is precipitated into pentane, and dried at 0.1 mm Hg for 48 hours to yield 8.65 g of a tan solid of the acidified form of polymer 6 shown in scheme B. Polymer 6 is analyzed and found to have the following properties:

$^1$H NMR ($\delta$, $d_8$-THF) 2.10 (s, 3H×0.83, $CH_3$) 6.4-7.1 (multiple peaks, 4H×0.83+2H×0.17, aromatic), 7.45 (s, 2H×0.17, aromatic), 8.0-12.0 (concentration dependent, broad, s, 1H× 0.17, NH), $^{19}$F NMR ($\delta$, $d_8$-THF) −78.24 (s, $CF_3$), $^{31}$P NMR ($\delta$, $d_8$-THF) −23 to −16 (broad multiple peaks, phosphazene phosphorus), $^{13}$C NMR ($\delta$, d8-THF) 21.0, 120.3 (q, $^1J_{CF}$=322 Hz), 121-123 (multiple peaks), 129-131 (multiple peaks), 133-135 (multiple peaks), 135.1, 149-151 (multiple peaks), 157.2. The (weight average) Mw=34,000 with PDI=2.1.

Elemental analysis of the polymer is: actual (calculated based on 17% sulfonimide side group); C, 50.56 (51.53); H, 3.70 (4.12); N, 5.55 (5.75); S, 6.28 (6.68); P, 9.61 (9.49); F, 6.09 (5.94); Cl, <0.10 (0.00); Na, 307 ppm (0 ppm).

Example 3

Synthesis of Sodium Fluoroalkoxy Cosubstituted Polymer as $(NP(OCH_2CF_3)_{1.50}(OC_6H_4SO_2NHSO_2CF_3)_{0.50})$ 4.0 gms poly(dichlorophosphazene) is dissolved in 400 ml THF, to which a solution of sodium fluoroalkoxide (0.87 gms 95% NaH reacted with 3.45 gms trifluoroethanol) in 50 ml THF to displace 50% of the chlorine atoms of the poly(dichlorophosphazene) and to form a reaction mixture. Then, a suspension formed of 6.02 gms of $NaOC_6H_4SO_2NNaSO_2CF_3$ in 50 ml THF is added to the reaction mixture and stirred at room temperature for 48 hours to produce a partially substituted polymer intermediate in solution. The remaining chlorine atoms are displaced by treatment of the polymer solution with 50 ml of a sodium fluoroalkoxide solution, prepared identical to that above, at room temperature. After 24 hours, the reaction mixture is concentrated by rotary evaporation to generate a viscous liquid. The viscous liquid is precipitated into concentrated HCl and dialyzed against (50/50 methanol/isopropanol). The dialyzed solution is concentrated again by rotary evaporation, and precipitated concentrated HCl to form a precipitate of polymer that is air dried. Further purification proceeds via precipitation into pentane, heptane, or hexane, followed by drying.

Example 4

Sulfonimide Functionalized Polyphosphazene in Silicate Matrix 1 gm of a sulfonimide functionalized polyphosphazene bearing the formula $(NP(OC_6H_4CH_3)_{1.50}(OC_6H_4SO_2NHSO_2CF_3)_{0.50})$ is dissolved in 5 ml dimethyl formamide (DMF) with 0.056 gms of the sol-gel precursor trifluoropropyl trimethoxy silane $(CF_3CH_2CH_2Si(OCH_3)_3)$. This is done in an argon atmosphere. The sample is stirred overnight under argon. Then 1 ml 0.1 M HCl solution is added to initiate cross-linking, and the solution is heated at 50° C. for 3 hours to facilitate the cross-linking. Following the 3 hour heating process, the solution is cooled to room temperature, poured into a Teflon well tray, and covered. The solution in the tray remains at room temperature and pressure for 1 hour, after which it is transferred to a vacuum oven for drying at room temperature under vacuum for 24 hours. Any sol-gel produced is then heated at 60° C. for 48 hours, followed by cooling to room temperature. After removal from the Teflon well tray, the resultant film is soaked in deionized water for a period of 48 hours to remove any excess DMF or small molecule impurities. The films are then removed from the water soak and dried.

Example 5

Membranes Of Polymer 6

Membranes of polymer 6 are solution-cast from 1,4-dioxane as 10% solutions 10 (w/v) onto a poly(propylene) plate and the 1,4-dioxane solvent allowed to evaporate at room temperature and pressure for 48 hours. The resulting membranes are dried under vacuum at 50° C. for an additional 48 hours. The membranes are crosslinked by exposure to $^{60}$Co-γ radiation.

Example 6

Membranes of Polymer Blends

Membranes of 75% polymer 6 (w/w) and 25% PVDF (w/w) blends are solution-cast from DMAC as 10% solutions (w/v) onto a poly(propylene) plate and dried in a vacuum oven under vacuum at room temperature for 24 hours and then further dried under vacuum at 65° C. for 72 hours. The dried membranes are then soaked in water for 24 hours, with the water replaced intermittently, followed by drying at 0.1 mm Hg at room temperature for 48 hours.

Example 7

Lithiated Sulfonimide Functionalized Polyphosphazenes 4 gms of a sulfonimide functionalized polyphosphazene bearing the formula $(NP(OCH_2CH_2OCH_2CH_2OCH_3)_{1.50}(OC_6H_4SO_2NHSO_2CF_3)_{0.50})$ is dissolved in 200 ml acidic water (pH 5) and dialyzed against 0.1 M LiCl solution for three days, changing the dialysis solution twice per day. This is followed by dialysis against deionized water for five days and against methanol for two days. The polymer is filtered, concentrated by rotary evaporator in the manner previously described, transferred to a storage vial, air dried for 24 hours and dried under vacuum at 60° C. for 48 hours.

Membrane Characterization

Characterization data for the cast membranes are given in Table 1. Ion-exchange capacities ("IEC") of the membranes are determined by placing a sample of known weight (approximately 0.1 g) of dry polymer in the acid form in 50 mL 2M aqueous NaCl. The sample is swirled intermittently for 48 hours. Three 10 mL aliquots are then removed and each of the aliquots is titrated with 0.01 M NaOH to a methyl red endpoint. The IEC of the polymer is calculated as the average IEC of the three aliquots using the equation:

$$IEC = ((x\ mL_{NaOH}) \cdot (0.01\ M_{NaOH}) \cdot (5)) \cdot (g\ dry\ weight\ of\ polymer)^{-1} = meq/g$$

The ion-exchange capacity (IEC) of the membrane of polymer 6, is 0.99 meq/g, which is equivalent to an acid content of 32% per polymer repeat unit. The acid content, calculated from the $^1$H NMR spectrum, is 34%. The equilibrium water swelling of an uncrosslinked membrane of polymer 6 of scheme B is 119% (based on membrane dry weight).

Crosslinking of the membrane of polymer 6 by $^{60}$Co γ-radiation caused a 40% and 65% reduction in water uptake after exposure to 20 and 40 Mrad radiation dosages, respectively. After crosslinking with 20 Mrad radiation, the conductivity of the polymer increased from 0.049 to 0.071 S/cm.

Proton conductivities in fully hydrated membranes are measured at room temperature by use of the well known four-electrode electrochemical impedance spectroscopy method. See, e.g., Journal of Electrochemical Society, Vol. 143, Issue 1 (1996), the teachings of which are incorporated herein by reference.

As shown in Table 1, a membrane formed from a blend of 75 wt %. polymer 6 and 25 wt. % PVDF, all amounts based on the total weight of the blend, gave results to those for the membrane formed from polymer 6 that is crosslinked by 40 Mrad $^{60}$Co-γ radiation.

TABLE 1

| Membrane | Membrane Thickness (cm) | IEC (meq/g) | Water Swelling (% H$_2$O/dry wt) | Proton Conductivity (S/cm) | Crosslinking (Mrad) |
|---|---|---|---|---|---|
| 6 | 0.013 | 0.99 | 119 | 0.049 | 0 |
| 6 | 0.011 | 0.99 | 73 | 0.071 | 20 |
| 6 | 0.009 | 0.99 | 42 | 0.058 | 40 |
| PVDF/6 Blend | 0.015 | — | 41 | 0.060 | 0 |
| Nafion 117 | 0.020 | 0.91 | 30 | 0.100 | 0 |

Membranes of functionalized polymer 6 blended with PVDF are fabricated by solution-casting from DMAC. The membranes are translucent when dry and transparent when hydrated, indicating true blend formation rather than a phase-separated mixture.

Improved polymer properties such as increased flexibility and decreased water swelling have been realized with membranes formed from blends of the functionalized polymers with other polymers. This makes the blended polymers suitable for use as proton conducting membranes for fuel cells (see Tables 2-3).

TABLE 2

Results of water swelling and proton conductivity measurements that reveal the effect of irradiation and blending
Phosphazene polymer IEC = 0.92 meq/g

| Blending composition (PVDF) | 0 | 0 | 0 | 0 |
|---|---|---|---|---|
| Radiation Dose (Mrads) | 0 | 10 | 20 | 40 |

TABLE 2-continued

Results of water swelling and proton conductivity measurements that reveal the effect of irradiation and blending
Phosphazene polymer IEC = 0.92 meq/g

| Water swelling (%) | 134 | 106 | 83 | 52 |
|---|---|---|---|---|
| Proton Conductivity (S/cm) | 0.044 | 0.045 | 0.042 | 0.035 |
| Blending composition (PVDF) | 20 | 20 | 20 | |
| Radiation Dose (Mrads) | 0 | 11 | 20 | |
| Water swelling (%) | 60 | 51 | 45 | |
| Proton Conductivity (S/cm) | 0.043 | 0.033 | 0.04 | |

TABLE 3

Results of water swelling and proton conductivity measurements that reveal the effect of irradiation and blending of sulfonimide polyphosphazenes with PVDF
Phosphazene polymer IEC = 0.92 meq/g

| Blending composition (PVDF) | 0 | 5 | 10 | 20 | 40 |
|---|---|---|---|---|---|
| Radiation Dose (Mrads) | 0 | 0 | 0 | 0 | 0 |
| Water swelling (%) | 134 | 72 | 63 | 60 | 16 |
| Proton Conductivity (S/cm) | 0.044 | 0.035 | 0.03 | 0.043 | 0.018 |
| Blending composition (PVDF) | 0 | 5 | 10 | 20 | 40 |
| Radiation Dose (Mrads) | 20 | 20 | 20 | 20 | 20 |
| Water swelling (%) | 83 | 78 | 61 | 45 | 16 |
| Proton Conductivity (S/cm) | 0.042 | 0.029 | 0.031 | 0.04 | 0.013 |

Fuel Cells

In another embodiment, a non-irradiated sulfonimide polyphosphazene (polymer 6) is cast into a membrane of 0.01 cm thickness. The membrane is treated with an ink that contains 20% Pt on carbon (Vulcan XC-72R), water, isopropanol and 5% Nafion solution in a mixture of lower aliphatic alcohols from Aldrich to ELAT/NC/D5/V2 carbon cloth with 20% wet proofing. The catalyst loading is 33 mg cm$^{-2}$ for both anode and cathode. The membrane electrode assembly is pressed at 65° C. and 400 PSI for 30 sec. The membrane electrode assembly is placed into an $H_2/O_2$ fuel cell from Fuel Cell Technologies, Inc. The $H_2$ and $O_2$ are humidified and preheated before entering the fuel cell.

In another aspect of this embodiment, the above procedure is repeated except the polymer is irradiated with 40 Mrad $^{60}$Co γ radiation. In yet another aspect of this embodiment, the above procedure employed with the non-irradiated polymer is repeated except that the membrane is formed from a blend of 80 wt. % polymer 6 with 20 wt. % (PVDF-HFP), all amounts based on total weight of the blend.

While the invention has been particularly shown and described with reference to preferred embodiments thereof it will be understood by those skilled in the art that various alterations in form and detail may be made therein without departing from the spirit and scope of the invention.

The invention claimed is:

1. A phenoxy sulfonimide functionalized polyphosphazene copolymer of the formula $[NP(ZR^2)_x (ZC_6H_4SO_2NR^1SO_2R_f)_{2-x}]_n$ where n is $\geq 3$ and where x is $\leq 2$, $R_f$ is a $C_1$-$C_8$ perfluoroalkyl, where $R^2$ is selected from the group consisting of —$CH_2CH_3$, —$C_6H_4CH_3$, —$CH_2CH_2OCH_2CH_2OCH_3$, —$CH_2CH_2OTHP$, —$C_6H_4COOPr$, —$CH_2CF_3$, —$CH_2CF_2OCF_2CF_2OCF_3$, —$C_6H_4CF_3$, —$C_6F_5$ and mixtures thereof, Z is O or NH, and $R^1$ is selected from the group consisting of Na, Li, H, and K where THP is tetrahydropyranyl.

2. The copolymer of claim 1 wherein $R^2$ is —$C_6H_4CH_3$, and Z is —O—.

3. The copolymer of claim 1 wherein $R^1$ is Na.

4. A method of making a phenoxy sulfonimide functionalized polyphosphazene copolymer of the formula $[NP(ZR^2)_x (ZC_6H_4SO_2NR^1SO_2R_f)_{2-x}]_n$, where n is $\geq 3$ and where x is $\leq 2$, $R_f$ is a $C_1$-$C_8$ perfluoroalkyl, where $R^2$ is selected from the group consisting of —$CH_2CH_3$, —$C_6H_4CH_3$, —$CH_2CH_2OCH_2CH_2OCH_3$, —$CH_2CH_2OTHP$ where THP is tetrahydropyranl, —$C_6H_4COOPr$, —$CH_2CF_3$, —$CH_2CF_2OCF_2CF_2OCF_3$, —$C_6H_4CF_3$, —$C_6F_5$, Z is O or NH, and $R^1$ is selected from the group consisting of Na, Li and K, comprising, reacting $(PNCl_2)_n$, where n$\geq 3$ with a first amount of compound of the formula $R^3R^2$ where $R^3$ is selected from the group consisting of —NaO, —LiO, —KO, $NH_2$ or mixtures thereof, $R^2$ is selected from the group consisting of —$CH_2CH_3$, —$C_6H_4CH_3$, —$CH_2CH_2OCH_2CH_2OCH_3$, —$CH_2CH_2OTHP$ where THP is tetrahydropyranyl, —$C_6H_4COOPr$, —$CH_2CF_3$, —$CH_2CF_2OCF_2CF_2OCF_3$, —$C_6H_4CF_3$, —$C_6F_5$, or mixtures thereof, with a second amount of a compound of the formula $R^2C_6H_4SO_2NHSO_2R_f$ where $R_f$ is a $C_1$-$C_8$ perfluoroalkyl, where $R^2$ is selected from the group consisting of —NaO, —LiO, —KO, NH or mixtures thereof, at a first temperature of about 60° C. to about 200° C. to produce a reaction product, reacting the reaction product with $R^3R^2$ at a second temperature of 60° C. to about 200° C. at a pressure of about 3.5-4 bar.

* * * * *